(12) United States Patent
Boy

(10) Patent No.: US 7,145,013 B2
(45) Date of Patent: Dec. 5, 2006

(54) 3-THIA-4-ARYLQUINOLIN-2-ONE DERIVATIVES

(75) Inventor: Kenneth M. Boy, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 192 days.

(21) Appl. No.: 10/963,889

(22) Filed: Oct. 13, 2004

(65) Prior Publication Data

US 2005/0080079 A1    Apr. 14, 2005

Related U.S. Application Data

(60) Provisional application No. 60/511,016, filed on Oct. 14, 2003.

(51) Int. Cl.
*C07D 215/16* (2006.01)
*C07D 215/20* (2006.01)

(52) U.S. Cl. ............... 546/153; 546/157; 514/312; 514/313

(58) Field of Classification Search ........ 546/153, 546/157; 514/312, 313
See application file for complete search history.

(56) References Cited

U.S. PATENT DOCUMENTS

| | | | |
|---|---|---|---|
| 5,892,045 A | 4/1999 | Sit et al. | |
| 5,922,735 A | 7/1999 | Sit et al. | |
| 5,972,961 A | 10/1999 | Hewawasam et al. | |
| 6,184,231 B1 | 2/2001 | Hewawasam et al. | |
| 6,353,119 B1 | 3/2002 | Crispino et al. | |
| 6,538,022 B1 | 3/2003 | Pollesello et al. | |

FOREIGN PATENT DOCUMENTS

| | | |
|---|---|---|
| JP | 2002371078 | 12/2002 |
| WO | WO 02/26713 A1 | 4/2002 |

OTHER PUBLICATIONS

Boy, Bioorganic & Medicinal Chemistry Letters, 14, pp. 5089-5093, 2004.*

* cited by examiner

*Primary Examiner*—D. Margaret Seaman
(74) *Attorney, Agent, or Firm*—James Epperson; Shah R. Makujina

(57) ABSTRACT

This invention describes compounds of Formula (I) which are modulators of potassium channels and are useful for treating conditions affected by abnormal potassium channel activity including erectile dysfunction and irritable bowel syndrome

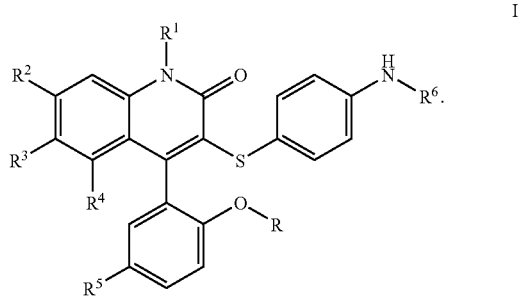

6 Claims, No Drawings

3-THIA-4-ARYLQUINOLIN-2-ONE DERIVATIVES

CROSS-REFERENCE TO RELATED APPLICATIONS

This application claims the benefit of U.S. Provisional Application Ser. No. 60/511,016 filed Oct. 14, 2003.

FIELD OF THE INVENTION

The present invention is generally directed to quinolinone derivatives, and more specifically directed to 3-thia-4-arylquinolin-2-one derivatives.

BACKGROUND OF THE INVENTION

Potassium channels are transmembrane proteins which are ubiquitously expressed in mammalian cells and represent one of the largest and the most diverse group of ion channels from a molecular perspective. Potassium channels play a key role in regulation of cell membrane potential and modulation of cell excitability. Potassium channels are largely regulated by voltage, cell metabolism, calcium and receptor mediated processes. [Cook, N. S., *Trends in Pharmacol. Sciences* 1988, 9, 21; and Quast, U., et al., *Trends in Pharmacol. Sciences* 1989, 10, 431]. Calcium-activated potassium ($K_{Ca}$) channels are a diverse group of ion channels that share a dependence on intracellular calcium ions for activity. The activity of $K_{Ca}$ channels is regulated by intracellular $[Ca^{2+}]$, membrane potential and phosphorylation. On the basis of their single-channel conductances in symmetrical $K^+$ solutions, $K_{Ca}$ channels are divided into three subclasses: large conductance (BK or Maxi-K) are those having a conductance of greater than about 150 picosemens (pS); intermediate conductance are those having a conductance of about 50–150 pS; and small conductance are those having a conductance of less than about 50 pS. Large-conductance calcium-activated potassium channels are present in many excitable cells including neurons, cardiac cells and various types of smooth muscle cells. [Singer, J. et al., *Pflugers Archiv.* 1987, 408, 98; Baro, I., et al., *Pflugers Archiv.* 1989, 414 (Suppl. 1), S168; and Ahmed, F. et al., *Br. J. Pharmacol.* 1984, 83, 227].

Potassium ions play a dominant role in controlling the resting membrane potential in most excitable cells and maintain the transmembrane voltage near the $K^+$ equilibrium potential ($E_k$) of about –90 milliVolts (mV). It has been shown that opening of potassium channels shift the cell membrane potential towards the $E_k$, resulting in hyperpolarization of the cell. [Cook, N. S., *Trends in Pharmacol. Sciences* 1988, 9, 21]. Hyperpolarized cells show a reduced response to potentially damaging depolarizing stimuli. Those BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells, as well as other types of cells, e.g., cardiac cells. [Xu, W., Liu, Y., Wang, S., McDonald, T., Van Eyk, J. E., Sidor, A., and O'Rourke, B. Cytoprotective Role of $Ca^{2+}$-activated $K^+$ Channels in the Cardiac Inner Mitochondrial Membrane. *Science* 2002, 298, 1029–1033].

BK channels have been shown to be one of two physiologically relevant potassium channels in relaxing human smooth muscle, including both intestinal and penile smooth muscle. Evidence that relaxation of smooth muscle is beneficial to irritible bowel syndrome and erectile dysfunction has been reported. See the following references: Christ, G. J. *Drug News Perspect.* 2000, 13, 28–36; Poynard T. et al. *Alimentary Pharmacology and Therapeutics* 2001, 15, 355–361; and Argentieri, T. M. U.S. patent application No. 2002/0183395.

A variety of synthetic and naturally occurring compounds with BK opening activity have been reported. 4-Aryl-3-hydroxyquinolin-2-one derivatives are disclosed in U.S. Pat. No. 5,892,045, issued Apr. 6, 1999; U.S. Pat. No. 5,922,735, issued Jul. 13, 1999; U.S. Pat. No. 6,353,119, issued Mar. 5, 2002. 4-Arylquinolin-2-one derivatives are disclosed in U.S. Pat. No. 6,184,231, published Feb. 6, 2001 and U.S. Pat. No. 5,972,961, published Oct. 26, 1999. See also Hewawasam, P. et. al. *J. Med. Chem.* 46 2819–2822 (2003). Other quinolinones are disclosed in U.S. Pat. No. 6,538,022; Japanese Pat. No. 2002371078; and PCT patent application WO 2002026713.

Despite advances in the art, further advances are needed for compounds capable of modulating potassium channels, in particular, large-conductance calcium-activated potassium channels. Such compounds would be useful in treating conditions arising from dysfunction of cellular membrane polarization and conductance.

SUMMARY OF THE INVENTION

This invention describes 3-thia-4-arylquinolin-2-one compounds having the general formula I or pharmaceutically acceptable salts or solvates thereof,

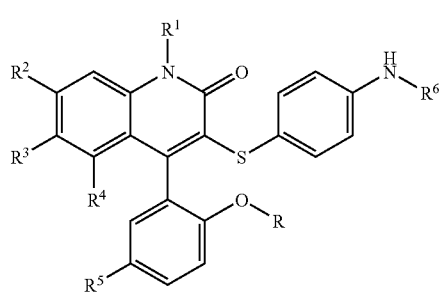

wherein R, $R^1$, $R^2$, $R^3$, $R^4$, $R^5$ and $R^6$ are as defined below.

The present invention also provides pharmaceutical compositions comprising these compounds and methods for the treatment of conditions responsive to potassium channel activity, such as ischemia, stroke, convulsions, epilepsy, asthma, irritable bowel syndrome, migraine, traumatic brain injury, spinal cord injury, sexual dysfunction and urinary incontinence.

DETAILED DESCRIPTION OF THE INVENTION

The present invention describes novel 3-thia-4-arylquinolin-2-one compounds and related derivatives of Formula (I) or pharmaceutically acceptable salts or solvates thereof

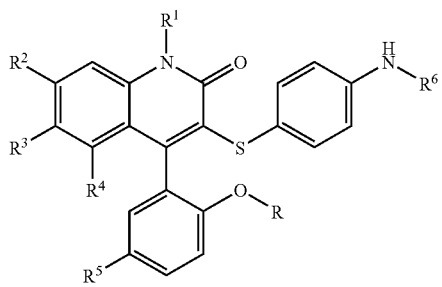

wherein:

R and $R^1$ are independently hydrogen or methyl;

$R^2$, $R^3$, and $R^4$ are independently hydrogen, halogen, cyano, nitro, or trifluoromethyl, provided $R^2$, $R^3$, and $R^4$ are not all hydrogen;

$R^5$ is bromo, chloro, or nitro;

$R^6$ is $SO_2R^7$;

$R^7$ is $C_{1-6}$alkyl, $C_{1-2}$fluoroalkyl, $C_{2-6}NR^8R^9$, or $NR^8R^9$;

$R^8$ and $R^9$ are independently hydrogen or $C_{1-6}$alkyl;

or $NR^8R^9$ taken together form a heterocycle selected from the group consisting of pyrrolidinyl, piperidinyl, 4-hydroxypiperidinyl, piperazinyl, 4-methylpiperazinyl, morpholinyl, and thiomorpholinyl.

The present invention also provides a method for the treatment or alleviation of disorders associated with BK channels, such as ischemia, stroke, convulsions, epilepsy, asthma, migraine, traumatic brain injury, spinal cord injury, sexual dysfunction, urinary incontinence and especially male erectile dysfunction and irritable bowel syndrome which comprises administering together with a conventional adjuvant, carrier or diluent a therapeutically effective amount of a compound of formula I or a pharmaceutically acceptable salt thereof.

The term "alkyl" includes both straight and branched chain alkyl groups. "Fluoroalkyl" means alkyl groups bearing from 1 to 5 fluorine atoms. Some examples of fluoroalkyl groups include monofluoromethyl, difluoromethyl, trifluoromethyl, 2,2,2-trifluoroethyl, and perfluoroethyl.

The term "atropisomer" refers to a stereoisomer resulting from restricted rotation about a single bond where the rotation barrier is high enough to permit isolation of the isomeric species.

The invention encompasses all stereoisomers and tautomers, including atropisomers. Examples of atropisomers and tautomers are shown below.

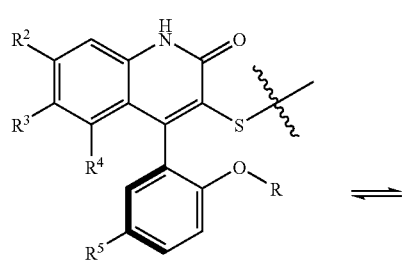

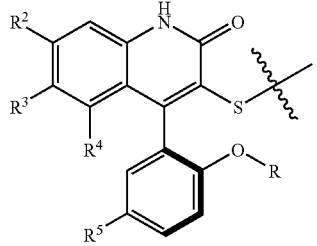

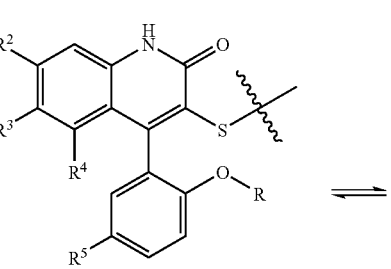

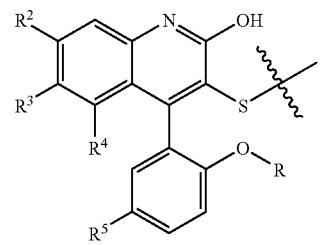

The terms "racemic mixture" and "racemate" refer to an equimolar or nearly equimolar mixture of two enantiomeric species. In addition, as used herein, the terms "racemic mixture" and "racemate" are intended to include equimolar mixtures of the two atropisomers.

The term "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445. Suitable inorganic bases such as alkali and alkaline earth metal bases include metallic cations such as sodium, potassium, magnesium, calcium and the like. The compounds of the present invention are useful in the form of the free base or acid or in the form of a pharmaceutically acceptable salt thereof. All forms are within the scope of the invention.

The term "halogen" as used herein and in the claims is intended to include fluorine, bromine, chlorine and iodine while the term "halide" is intended to include fluoride, bromide, chloride and iodide anion.

The term "therapeutically effective amount" means the total amount of each active component that is sufficient to show a meaningful patient benefit, i.e., amelioration of acute conditions characterized by openers of large conductance calcium-activated K+ channels or increase in the rate of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the invention", and equivalent expressions, are meant to embrace compounds of Formula I and include prodrugs, pharmaceutically acceptable salts, and solvates, e.g. hydrates. Similarly, reference to intermediates, whether or not they themselves are claimed, is meant to embrace their salts, and solvates, where the context so permits.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "patient" includes both human and other mammals.

The term "pharmaceutical composition" means a composition comprising a compound of the invention in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable risk/benefit ratio.

The term "pharmaceutically acceptable prodrugs" as used herein means those prodrugs of the compounds useful according to the present invention which are, within the scope of sound medical judgment, suitable for use in contact with the tissues of humans and lower animals without undue toxicity, irritation, allergic response, and the like, commensurate with a reasonable risk/benefit ratio, and effective for their intended use, as well as zwitterionic forms, where possible, of the compounds of the invention.

The term "prodrugs", as the term is used herein, are intended to include any covalently bonded carriers which release an active parent drug of the present invention in vivo when such prodrug is administered to a patient. Since prodrugs are known to enhance numerous desirable qualities of pharmaceuticals (i.e., solubility, bioavailability, manufacturing, etc.) the compounds of the present invention may be delivered in prodrug form. Thus, the skilled artisan will appreciate that the present invention encompasses prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to form the parent compound. The transformation in vivo may be, for example, as the result of some metabolic process, such as chemical or enzymatic hydrolysis of a carboxylic, phosphoric or sulphate ester, or reduction or oxidation of a susceptible functionality. Prodrugs include compounds of the present invention wherein a hydroxy, amino, or sulfhydryl group is bonded to any group that, when the prodrug of the present invention is administered to a patient, it cleaves to form a free hydroxyl, free amino, or free sulfydryl group, respectively. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups can act as prodrugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p. 309–396, 1985; A Textbook of Drug Design and Development, Krogsgaard-Larsen and H. Bundgaard, ed., Chapter 5; "Design and Applications of Prodrugs" p. 113–191, 1991; Advanced Drug Delivery Reviews, H. Bundgard, 8, p. 1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987.

One aspect of the invention are compounds of formula (I) where R is hydrogen.

Another aspect of the invention are compounds of formula (I) where $R^1$ is hydrogen.

Another aspect of the invention are compounds of formula (I) where $R^2$ is hydrogen, $R^3$ is trifluoromethyl, and $R^4$ is hydrogen.

Another aspect of the invention are compounds of formula (I) where $R^5$ is chloro.

Some compounds of the invention include

3-[(4-aminophenyl)thio]-4-(5-chloro-2-hydroxyphenyl)-6-(trifluoromethyl)-2(1H)-quinolinone;

3-[(4-aminophenyl)thio]-4-(5-chloro-2-hydroxyphenyl)-1-methyl-6-(trifluoromethyl)-2(1 H)-quinolinone;

N-[4-[[4-(5-chloro-2-hydroxyphenyl)-1,2-dihydro-2-oxo-6-(trifluoromethyl)-3-quinolinyl]thio]phenyl]ethanesulfonamide;

N-[4-[[4-(5-chloro-2-methoxyphenyl)-1,2-dihydro-2-oxo-6-(trifluoromethyl)-3-quinolinyl]thio]phenyl]-1,1,1-trifluoromethanesulfonamide;

N-[4-[[4-(5-chloro-2-hydroxyphenyl)-1,2-dihydro-2-oxo-6-(trifluoromethyl)-3-quinolinyl]thio]phenyl]-1-propanesulfonamide;

N'-[4-[[4-(5-chloro-2-hydroxyphenyl)-1,2-dihydro-2-oxo-6-(trifluoromethyl)-3-quinolinyl]thio]phenyl]-N,N-dimethylsulfamide;

N-[4-[[4-(5-chloro-2-hydroxyphenyl)-1,2-dihydro-2-oxo-6-(trifluoromethyl)-3-quinolinyl]thio]phenyl]-1,1,1-trifluoromethanesulfonamide;

N-[4-[[4-(5-chloro-2-hydroxyphenyl)-1,2-dihydro-2-oxo-6-(trifluoromethyl)-3-quinolinyl]thio]phenyl]-2,2,2-trifluoroethanesulfonamide;

N'-[4-[[4-(5-chloro-2-hydroxyphenyl)-1,2-dihydro-1-methyl-2-oxo-6-(trifluoromethyl)-3-quinolinyl]thio]phenyl]-N,N-dimethylsulfamide; and N-[4-[[4-(5-chloro-2-hydroxyphenyl)-1,2-dihydro-2-oxo-6-(trifluoromethyl)-3-quinolinyl]thio]phenyl]-4-morpholinepropanesulfonamide;

and salts and solvates thereof.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

Synthetic Methods

The compounds of Formula I may be prepared by various procedures such as those illustrated herein in the examples and in the Reaction Schemes described in the specific embodiments and variations thereof which would be evident to those skilled in the art.

The following reaction schemes illustrate representative general procedures for the preparation of intermediates and methods for the preparation of compounds of Formula I according to this invention. It should also be evident to those skilled in the art that appropriate substitution of both the materials and methods disclosed herein will produce the examples illustrated below and those encompassed by the scope of this invention.

Scheme 1.

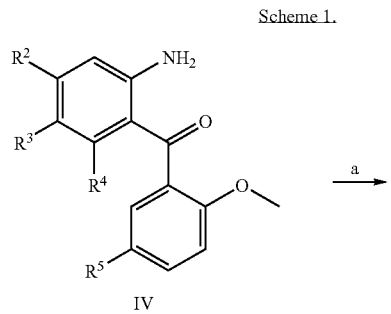

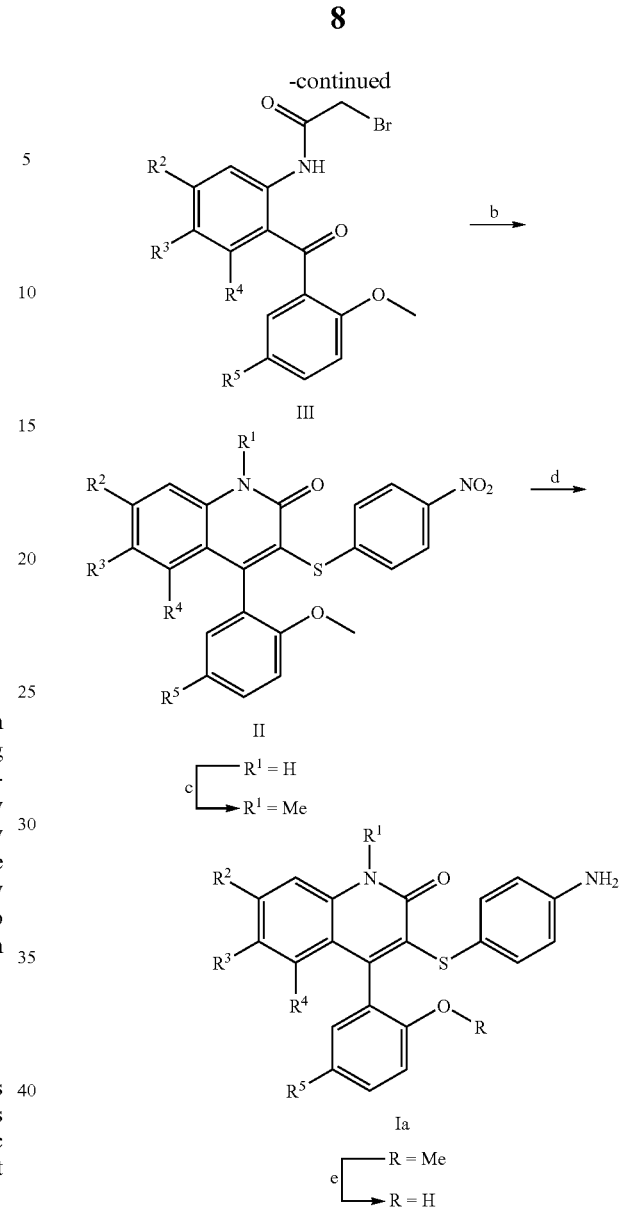

Reagents and conditions: (a) bromoacetyl bromide, pyridine, CH$_2$Cl$_2$, 0° C.; (b) NaH, p-nitrothiophenol, III, 0° C. to r.t.; (c) NaOMe, MeI, THF; (d) SnCl$_2$, EtOH, reflux; (e) BBr$_3$, CH$_2$Cl$_2$, −78° C. to r.t.

Scheme 2.

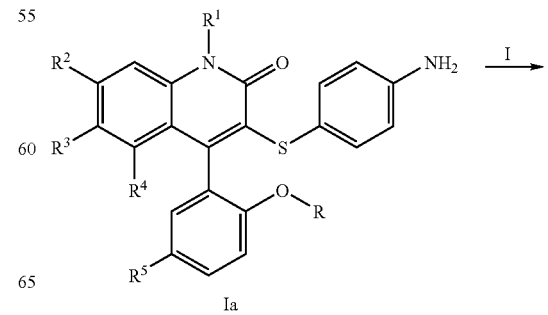

-continued

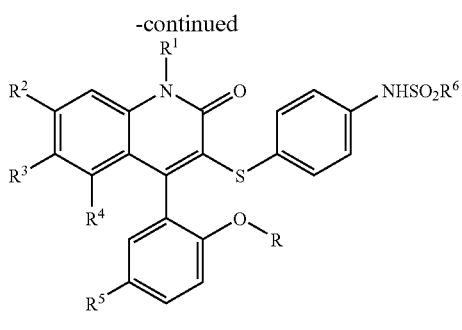

Ib

Reagents and conditions: (1) RSO₂Cl, CH₂Cl₂, pyridine, r.t. or 80° C.

Biological Methods

Openers of BK channels exert their cellular effects by increasing the open probability of these channels [Gribkoff, V. K., et al., Neuroscientist, 7:166–177 (2001); Gribkoff, V. K. et al., Adv. Pharmacol., 37:319–348 (1997); McKay, M. C., et al., J. Neurophysiol., 71: 1873–1882 (1994); and Olesen, S.-P., Exp. Opin. Invest. Drugs, 3: 1181–1188 (1994)]. This increase in the opening of individual BK channels collectively results in the hyperpolarization of cell membranes, particularly in depolarized cells, produced by significant increases in whole-cell BK-mediated conductance. Hyperpolarization, in turn, reduces the excitability of nerve and muscle cells, and decreases the open probability of voltage-dependent $Ca^{2+}$ channels, effectively lowering intracellular concentrations of this potentially harmful cation. The effect on smooth muscle is that of relaxation.

Assay for BK Channel Openers

The ability of the compounds of the invention to open BK channels and increase whole-cell outward ($K^+$) BK-mediated currents was assessed under voltage-clamp conditions by determining their ability to increase cloned mammalian (mSlo or hSlo) BK-mediated outward current heterologously expressed in Xenopus oocytes [Butler, A., et al., Science 1993, 261, 221–224; Dworetzky, S. I., et al., Mol. Brain Res. 1994, 27, 189–193; Gribkoff, V. K., et al., Mol. Pharmacol. 1996, 50, 206–217]. The two BK constructs employed represent nearly structurally identical homologous proteins, and have proven to be pharmacologically indistinguishable in our tests. To isolate BK current from native (background, non-BK) current, the specific and potent BK channel-blocking toxin iberiotoxin (IBTX) [Galvez, A., et al., J. Biol. Chem. 1990, 265, 11083–11090] was employed at a supramaximal concentration, e.g., 50–100 nanomolar ("nM"). The relative contribution of BK channel-mediated current to total outward current was determined by subtraction of the current remaining in the presence of IBTX (non-BK current) from the current profiles obtained in all other experimental conditions (control, drug, and wash) [Gribkoff, V. K. et al., Mol. Pharmacol. 1996, 50, 206–217]. It was determined that at the tested concentrations the compounds profiled did not significantly effect non-BK native currents in the oocytes. All compounds were tested in 5–10 oocytes and are reported at the indicated concentration of 20 micromolar ("µM") (or as otherwise indicated); the effect of the selected compounds of the invention on BK current was expressed as the percent of control IBTX-sensitive current at a single transmembrane voltage (+140 mV) and is listed in Table 1. Recordings were accomplished using standard two-electrode voltage clamp techniques [Stuhmer, W., et al., Methods in Enzymology, 1992, 207, 319–339]; voltage-clamp protocols consisted of 500–750 milliseconds ("ms") duration step depolarizations, from a holding potential of −60 mV, to a final voltage up to +140 mV in 20 mV steps. The experimental media (modified Barth's solution) consisted of millimolar ("mM"): NaCl (88), NaHCO₃ (2.4), KCl (1.0), HEPES (10), MgSO₄ (0.82), Ca(NO₃)₂ (0.33), CaCl₂ (0.41); pH 7.5.

Rat Small Intestine

The ability of the compounds of the invention to relax rat small intestine tissue as a model for the treatment of irritable bowel syndrome is described as follows. Male rats (Harlan, Sprague Dawley, 250–350 g) were sacrificed by decapitation. A portion of small intestine (ileum) was removed and the attached connective tissues and intestinal contents removed. The ileum was cut into segments of ≦1 cm in length. The segments were mounted longitudinally between fixed hooks in organ baths containing warm (37° C.) physiological salt solution (composition in mM: NaCl 118.4, KCl 4.7, KH₂PO4 1.2, MgSO₄ 1.2, CaCl₂ 1.8, Glucose 10.1, NaHCO₃ 25; gassed with 95% O₂/5% CO₂, pH 7.4). A stable tension of ~1.5 g was maintained in the tissue segments during the equilibration period of 45 minutes. Changes in muscle tension were measured with isometric force transducers (Grass, FT-03C) and recorded using AcqKnowledge data acquisition system (AcqKnowledge for MP100WS, Biopac Systems Inc., Goleta, Calif.). Compound or vehicle was added in the baths for 30 minutes. "Zero" active force was established at the end of the experiment using nifedipine (20 µM). The effects of compounds or vehicle on force was determined by measuring the integral of nifedipine-sensitive force (including resting tone and spontaneous contractions) pre- and 30 min post-compound (or vehicle) addition. Results are expressed as the percentage inhibition of force. DMSO vehicle inhibited force (integral) by −0.6±3.0% (n=25). Results are summarized in Table 1.

Rabbit Corpus Cavernosum

The ability of the compounds of the invention to relax rabbit corpus cavernosum tissue as a model for the treatment of erectile dysfunction is described as follows. New Zealand white rabbits (3.4–3.7 kg) were euthanized by sodium pentobarbital (100 mg/kg) overdose. The penis from each animal was rapidly removed and immersed in a cold oxygenated modified Krebs Henseleit bicarbonate buffer. The penis' outer tunica was removed and the corpus cavernosum smooth muscle obtained and cut into strips approximately 3–5 mm long. The strips were suspended in tissue baths containing physiological salt solution (see above), and allowed to equilibrate for at least one hour under resting tension of 1.0 gram. Isometric force was measured as described above. Tissue strips were stimulated with the (x-agonist phenylephrine (3 µM) and allowed to reach a steady level of force prior to the addition of test compounds. The results are expressed as the percentage inhibition of phenylephrine-induced force as compared to vehicle control. Results are summarized in Table 1.

TABLE 1
| Ex | Structure | % MaxiK opening * | % Inhibition of force (RCC strips) | % Inhibition of force (RSI strips) |
|---|---|---|---|---|
| 1 | 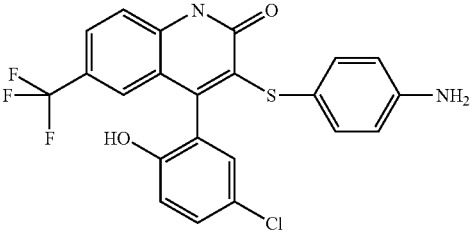 | 392 | 27 | 10 |
| 2 | 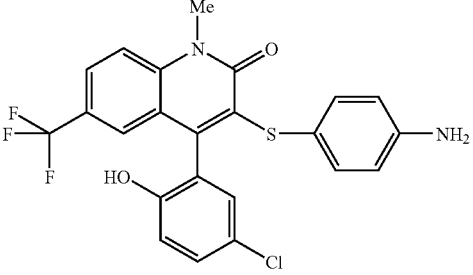 | 144 | 7 | |
| 3 | 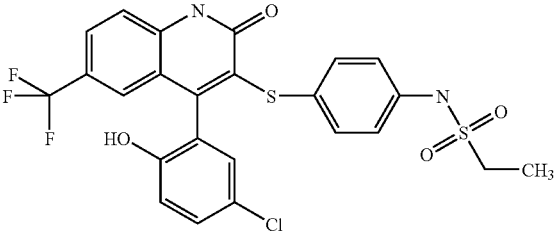 | 296 | | |
| 4 | 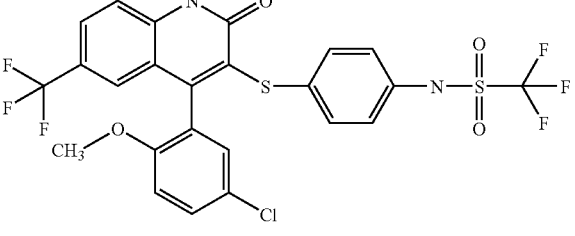 | 235 | 21 | |
| 5 | 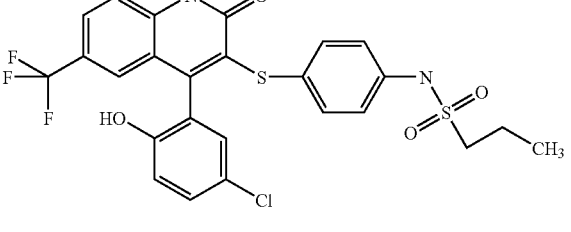 | 255 | | |

TABLE 1-continued

| Ex | Structure | % MaxiK opening * | % Inhibition of force (RCC strips) | % Inhibition of force (RSI strips) |
|---|---|---|---|---|
| 6 | 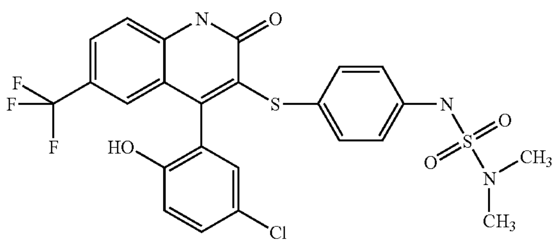 | 222◊ | | |
| 7 | 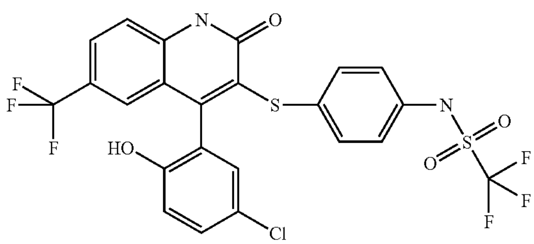 | 277 | 32 | 51 |
| 8 | 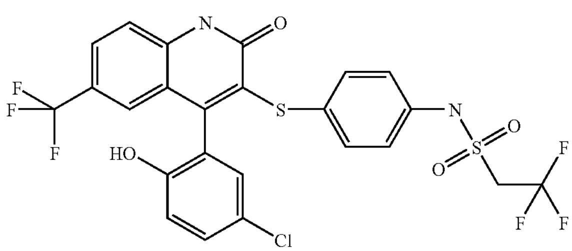 | 170 | | |
| 9 | 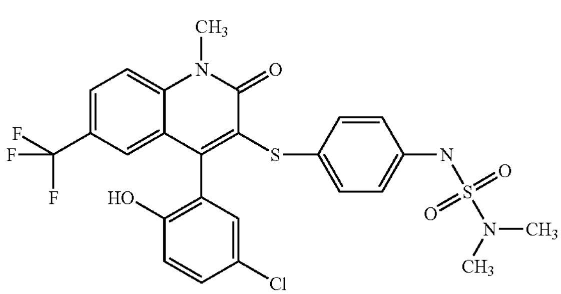 | 114◊ | | |
| 10 | 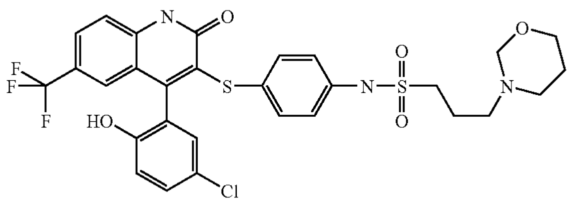 | 354 | 35 | |

*at 20 μM (unless otherwise indicated) expressed as percent increase over BK current in controls, voltage step to +140 mV
◊ at 1 μM.

The results of the above biological tests demonstrate that the compounds of the invention are potent openers of large-conductance calcium-activated K$^+$ channels (BK or Maxi-K channels) and are effective at relaxing intestinal and penile smooth muscle.

Pharmaceutical Compositions and Methods of Use

The compounds of the present invention are useful for the treatment of patients for conditions arising from dysfunction of cellular membrane polarization and conductance and are indicated for the treatment of ischemia, stroke, convulsions, epilepsy, asthma, migraine, traumatic brain injury, spinal cord injury, sexual dysfunction, urinary incontinence and especially male erectile dysfunction and irritable bowel syndrome, as well as other disorders sensitive to BK channel activity. Accordingly, in one aspect of the present invention, there is provided a method of treatment or prevention of conditions responsive to opening of potassium channels in a patient in need thereof, which comprises administering to the patient a therapeutically effective amount of a compound of Formula I or a pharmaceutically acceptable salt, solvate or prodrug thereof. In another aspect, this invention provides a method for the treatment of or protection from disorders which are mediated by opening of the large conductance calcium-activated K$^+$ channels in a patient in need thereof, which comprises administering to the patient a therapeutically effective amount of a compound of Formula I or a pharmaceutically acceptable salt, solvate or prodrug thereof. Preferably, the compounds of Formula I are useful in the treatment of ischemia, stroke, convulsions, asthma, irritable bowel syndrome, migraine, traumatic brain injury, urinary incontinence, irritable bowel syndrome, and sexual dysfunction in both men (erectile dysfunction, for example, due to diabetes mellitus, spinal cord injury, radical prostatectomy, psychogenic etiology or any other cause) and women by improving blood flow to the genitalia, especially the corpus cavernosum, and other disorders sensitive to BK channel activating activity.

In another aspect, this invention provides pharmaceutical compositions comprising at least one compound of Formula I and a carrier.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.01 micrograms per kilogram (μg/kg) to 50 milligrams per kilogram (mg/kg) body weight and preferrably, from about 0.1 μg/kg to 5 mg/kg body weight for oral administration. For parenteral administration, the dose may be in the range of 0.1 μg/kg to 1 mg/kg body weight for intravenous administration. The active ingredient will preferably be administered in equal doses from one to four times a day. However, usually a small dosage is administered, and the dosage is gradually increased until the optimal dosage for the host under treatment is determined.

The compounds of the present invention may be employed alone or in combination with other suitable therapeutic agents useful in the treatment of the dysfunction of cellular membrane polarization and conductance, e.g., sexual dysfunction such as cyclic guamine monophosphate, phosphodiaterase (cGMP PDE) inhibitors and particularly cGMP PDE V inhibitors such as sildenafil. Exemplary of the therapeutic agents are PDE V inhibitors selected from imidazo-quinazolines (see WO 98/08848), carbazoles (see WO 97/03675, WO 97/03985 and WO 95/19978), imidazopurinones (see WO 97/19947), benzimidazoles (see WO 97/24334), pyrazoloquinolines (see U.S. Pat. No. 5,488, 055), anthranilic acid derivatives (see WO 95/18097), fused heterocycles (see WO 98/07430) and thienopyrimidines (see DE 19632423). Alosetron hydrochloride can be combined with the compounds of the present invention to treat irritable bowel syndrome (see, e.g., U.S. Pat. Nos. 5,360,800 and 6,284,770).

The amount of compound actually administered will be determined by a physician using sound medical judgement.

DESCRIPTION OF SPECIFIC EMBODIMENTS

The following examples are given by way of illustration and are not to be construed as limiting the scope of the claims which follow.

In the following examples, all temperatures are given in degrees Centigrade. Melting points were recorded on a Gallenkamp capillary melting point apparatus are uncorrected. Proton magnetic resonance ($^1$H NMR) spectra were recorded on a Bruker AC 300 or 500 megaHertz ("MHz")

spectrometer. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 $cm^{-1}$ to 400 $cm^{-1}$, calibrated to 1601 $cm^{-1}$ absorption of a polystyrene film and reported in reciprocal centimeters ($cm^{-1}$). Low resolution mass spectra (MS) and the apparent molecular weight ($MH^+$) or $(M-H)^-$ was determined on a Finnigan TSQ 7000. LC-MS analysis were carried out on a Shimadzu instrument using one of the following methods (1) YMC ODS C18 column (4.6×33 mm) employing a 4 min linear gradient of 0% to 100% solvent B in A and a 1 min hold at 100% B (2) YMC ODS C18 column (4.6×30 mm) employing a 2 min linear gradient of 0% to 100% solvent B in A and a 1 min hold at 100% B (3) YMC ODS C18 column (3.0×50 mm) employing a 2 min linear gradient of 0% to 100% solvent B in A and a 1 min hold at 100% B (4) YMC ODS. C18 column (3.0×50 mm) employing a 4 min linear gradient of 0% to 100% solvent B in A and a 1 min hold at 100% B. In all cases solvent A: 10% methanol, 90% water, 0.1% TFA; and solvent B: 90% methanol, 10% water, 0.1% TFA with UV detector set at 220 nm. The element analyses are reported as percent by weight. Unless otherwise indicated in the Specific Embodiments, $R^2$ and $R^4$ are H in the descriptive title of the Examples.

Intermediates of Formula (III)

Intermediate 1

2-Bromo-N-[2-(5-chloro-2-methoxy-benzoyl)-4-trifluoromethyl-phenyl]-acetamide. To a solution of (2-Amino-5-trifluoromethyl-phenyl)-(5-chloro-2-methoxy-phenyl)-methanone (IV) (14.13 g, 42.9 mmol, 1 eq) in Dichloromethane (120 mL) at 0° C. was added pyridine (4.65 mL, 57.5 mmol, 1.34 eq), then Bromoacetyl bromide (4.98 mL, 57.2 mmol, 1.33 eq). After 3 h, the reaction was quenched with Sodium bicarbonate (aq) and extracted three times into Dichloromethane. The combined organic layers were dried over Magnesium sulfate, filtered and concentrated in vacuo. The product was used without further purification.

$^1$H NMR (300 MHz, CDCl3) δ 12.18 (s, 1H), 8.88 (d, J=8.9 Hz, 1H), 7.82 (dd, J=1.9, 8.9 Hz, 1H), 7.71 (d, J=1.9 Hz, 1H), 7.51 (dd, J=2.6, 8.9 Hz, 1H), 7.41 (d, J=2.6 Hz, 1H), 6.97 (d, J=8.9 Hz, 1H), 4.08 (s, 2H), 3.70 (s, 3H).

Intermediates of Formula (II)

Intermediate 2

4-(5-Chloro-2-methoxy-phenyl)-3-(4-nitro-phenylsulfanyl)-6-trifluoromethyl-1H-quinolin-2-one. To a solution of 4-nitrothiophenol (8.73 g, 56.3 mmol, 2.5 eq) in THF (140 mL) at 0° C. was added Sodium hydride (2.26 g, 60% dispersion in mineral oil, 56.5 mmol, 2.5 eq). After stirring for 15 min, a solution of III (10.15 g, 22.5 mmol, 1 eq) in THF (50 mL) was added rapidly dropwise to the blood-red solution. After 5 min, the ice bath was removed, and the solution stirred for 3 h at room temperature. The reaction was quenched with 1 M HCl, and extracted three times into EtOAC. The combined organic layers were dried over Magnesium sulfate, filtered, and concentrated in vacuo. Chromatography (2:1, 1:1 Hexane:EtOAc) provided pure II in quantitative yield.

$^1$H NMR (300 MHz, CDCl3) δ 12.64 (s, 1H), 8.06 (d, J=8.9 Hz, 2H), 7.68 (d, J=7.1 Hz, 1H), 7.47 (dd, J=2.6, 8.9 Hz, 1H), 7.38–7.31 (m, 4H), 7.12 (d, J=2.6 Hz, 1H), 6.97 (d, J=8.9 Hz, 1H), 3.64 (s, 3H).

Intermediate 3

4-(5-Chloro-2-methoxy-phenyl)-1-methyl-3-(4-nitrophenylsulfanyl)-1H-quinolin-2-one. To a suspension of NaOMe (64 mg, 1.2 mmol) in THF (10 mL) was added II (R1=H) (500 mg, 0.99 mmol). The mixture was stirred for 0.5 h at room temperature, at which time methyl iodide (760 μL, 12 mmol) was added. After 18 h, the mixture was concentrated in vacuo. Brine and ethyl acetate were added, and the mixture extracted three times with ethyl acetate. The organic extracts were dried over magnesium sulfate, concentrated in vacuo, and purified by silica gel chromatography to provide pure II (R1=Me), (350.4 mg, 68% yield).

EXAMPLE 1

3-[(4-Aminophenyl)thio]-4-(5-chloro-2-hydroxyphenyl)-6-(trifluoromethyl)-2(1H)-quinolinone. To a solution of II (2.07 g, 4.09 mmol, 1 eq) in EtOH (21. mL) was added SnCl2 (4.56 g, 24.0 mmol, 5.9 eq), and the resulting suspension heated to reflux for 3 h. After cooling to room temperature, the mixture was added to ice, and Sodium bicarbonate was added. The mixture was filtered, extracted to EtOAc, and dried over Magnesium sulfate. Concentration in vacuo followed by recrystallization in EtOAc/Hexane provided Ia (1.28 g, 66%).

EXAMPLE 2

3-[(4-Aminophenyl)thio]-4-(5-chloro-2-hydroxyphenyl)-1-methyl-6-(trifluoromethyl)-2(1H)-quinolinone. To a solution of Ia (R=Me) (509 mg, 1.07 mmol, 1 eq) in methylene chloride (30 mL) at −78° C. was added a 1M solution of boron tribromide in methylene chloride (6 mL, 6 mmol, 5.6 eq). The solution was brought to room temperature and stirred for 60 h. The solution was cooled to −78° C. and quenched with saturated aqueous sodium bicarbonate, extracted with ethyl acetate, dried over magnesium sulfate, and concentrated in vacuo. Silica gel chromatography (ethyl acetate, then methanol/methylene chloride) provided the desired material Ia (R=H).

EXAMPLE 3

N-[4-[[4-(5-Chloro-2-hydroxyphenyl)-1,2-dihydro-2-oxo-6-(trifluoromethyl)-3-quinolinyl]thio]phenyl]ethanesulfonamide. To a solution of 3-(4-Amino-phenylsulfanyl)-4-(5-chloro-2-methoxy-phenyl)-6-trifluoromethyl-1H-quinolin-2-one or 3-(4-Amino-phenylsulfanyl)-4-(5-chloro-2-hydroxy-phenyl)-6-trifluoromethyl-1H-quinolin-2-one (49.0 mg, 103 μmol, 1 eq) in pyridine (50 μL) and methylene chloride (500 μL) was added the appropriate sulfonyl chloride (422 μmol, 4.1 eq), and the mixture stirred overnight at room temperature, or at 80° C. in the absence of methylene chloride for difficult cases. The pyridine was removed in vacuo, and 4 N NaOH was added. The suspension was diluted with water, washed with chloroform, and adjusted to pH 5 with 1 M HCl. The product was extracted into a mixture of EtOAc and methylene chloride, dried with Magnesium sulfate, and concentrated in vacuo. Final purification was effected by reverse phase HPLC to afford pure Ib. $^1$H NMR (300 MHz, CDCl3) δ 11.04 (s, 1H), 8.90 (s, 1H), 7.67 (d, J=8.6 Hz, 1H), 7.43 (s, 1H), 7.40–7.30 (m, 2H), 7.30–7.24 (m, 3H), 7.11 (d, J=2.5 Hz, 1H), 6.98 (d, J=8.7 Hz, 1H), 6.91 (d, J=8.7 Hz, 2H), 2.99 (q, J=7.4 Hz, 2H), 1.21 (t, J=7.4 Hz, 3H); LCMS (M+H) 555, RT=3.177 (Method 1).

Examples 4–10 were prepared by similar methods.

| Example | Structure | Retention time (min) | HPLC Method ** | MS (M$^+$) |
|---|---|---|---|---|
| 4 | 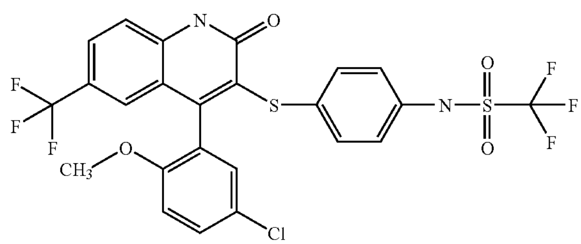 | 3.780 | 1 | 609 |
| 5 | 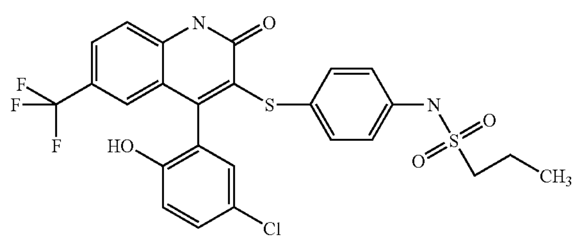 | 3.353 | 1 | 569 |
| 6 | 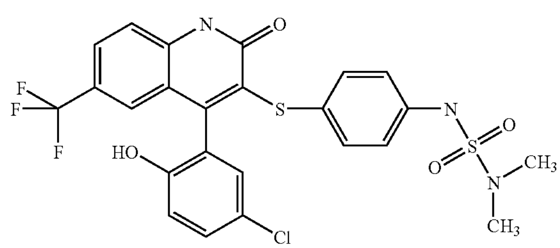 | 3.233 | 1 | 570 |
| 7 | 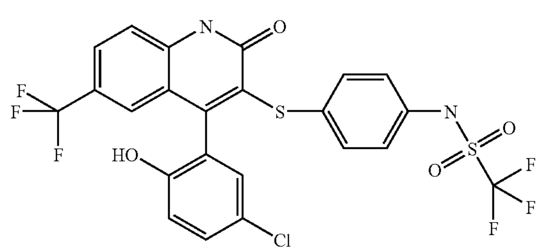 | 3.510 | 1 | 595 |
| 8 | 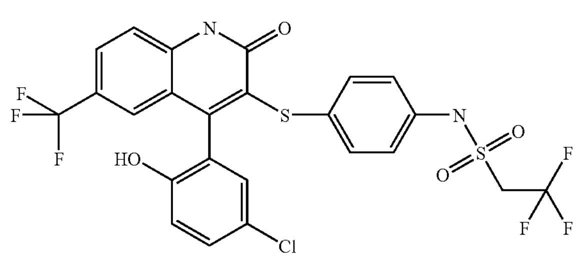 | 3.320 | 1 | 609 |

| Example | Structure | Retention time (min) | HPLC Method ** | MS (M+) |
|---------|-----------|----------------------|----------------|---------|
| 9 | 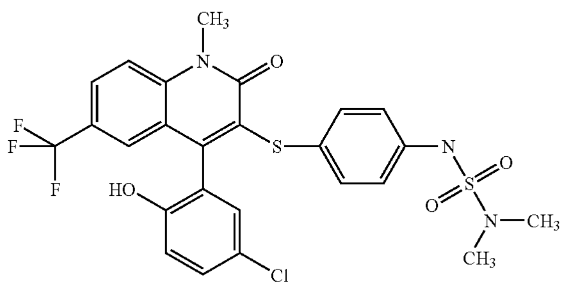 | 3.253 | 1 | 584 |
| 10 | 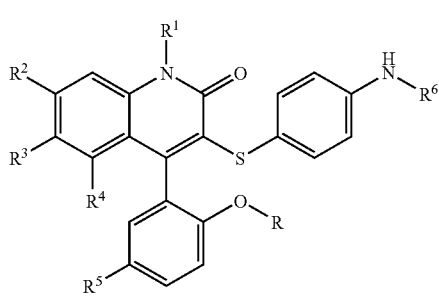 | 3.590 | 1 | 654 |

** (1) YMC ODS C18 column (4.6 × 33 mm) employing a 4 min linear gradient of 0% to 100% solvent B in A and a 1 min hold at 100% B (2) YMC ODS C18 column(4.6 × 30 mm) employing a 2 min linear gradient of 0% to 100% solvent B in A and a 1 min hold at 100% B (3) YMC ODS C18 column (3.0 × 50 mm) employing a 2 min-linear gradient of 0% to 100% solvent B in A and a 1 min hold at 100% B (4) YMC ODS C18 column (3.0 × 50 mm) employing a 4 min linear gradient of 0% to 100% solventB in A and a 1 min hold at 100% B. In all cases solvent A: 10% methanol, 90% water, 0.1% TFA; and solvent B: 90% methanol, 10% water, 0.1% TFA with UV detector set at 220 nm.

Although the invention has been described with respect to specific aspects, those skilled in the art will recognize that other aspects are intended to be included within the scope of the claims which follow. Other substituents substantially equivalent to the specific substituents described herein, e.g., R, $R^1$, $R^2$, $R^3$, $R^4$, $R^5$, can be employed within the scope of the invention.

What is claimed is:

1. A compound of Formula (I)

I wherein:
R and $R^1$ are independently hydrogen or methyl;
$R^2$, $R^3$, and $R^4$ are independently hydrogen, halogen, cyano, nitro, or trifluoromethyl, provided $R^2$, $R^3$, and $R^4$ are not all hydrogen;
$R^5$ is bromo, chloro, or nitro;
$R^6$ is $SO_2R^7$;
$R^7$ is $C_{1-6}$alkyl, $C_{1-2}$fluoroalkyl, $C_{2-6}NR^8R^9$, or $NR^8R^9$;
$R^8$ and $R^9$ are independently hydrogen or $C_{1-6}$alkyl;
or $NR^8R^9$ taken together form a heterocycle selected from the group consisting of pyrrolidinyl, piperidinyl, 4-hydroxypiperidinyl, piperazinyl, 4-methylpiperazinyl, morpholinyl, and thiomorpholinyl;
or a pharmaceutically acceptable salt or solvate thereof.

2. A compound of claim 1 where $R^2$ is hydrogen, $R^3$ is trifluoromethyl, and $R^4$ is hydrogen.

3. A compound of claim 1 where R is hydrogen.

4. A compound of claim 1 where $R^1$ is hydrogen.

5. A compound of claim 1 where $R^5$ is chloro.

6. A compound of claim 1 selected from the group consisting of
N-[4-[[4-(5-chloro-2-hydroxyphenyl)-1,2-dihydro-2-oxo-6-(trifluoromethyl)-3-quinolinyl]thio]phenyl]ethanesulfonamide;
N-[4-[[4-(5-chloro-2-methoxyphenyl)-1,2-dihydro-2-oxo-6-(trifluoromethyl)-3-quinolinyl]thio]phenyl]-1,1,1-trifluoromethanesulfonamide;
N-[4-[[4-(5-chloro-2-hydroxyphenyl)-1,2-dihydro-2-oxo-6-(trifluoromethyl)-3-quinolinyl]thio]phenyl]-1-propanesulfonamide;
N'-[4-[[4-(5-chloro-2-hydroxyphenyl)-1,2-dihydro-2-oxo-6-(trifluoromethyl)-3-quinolinyl]thio]phenyl]-N,N-dimethylsulfamide;
N-[4-[[4-(5-chloro-2-hydroxyphenyl)-1,2-dihydro-2-oxo-6-(trifluoromethyl)-3-quinolinyl]thio]phenyl]-1,1,1-trifluoromethanesulfonamide;

N-[4-[[4-(5-chloro-2-hydroxyphenyl)-1,2-dihydro-2-oxo-6-(trifluoromethyl)-3-quinolinyl]thio]phenyl]-2,2,2-trifluoroethanesulfonamide;

N'-[4-[[4-(5-chloro-2-hydroxyphenyl)-1,2-dihydro-1-methyl-2-oxo-6-(trifluoromethyl)-3-quinolinyl]thio]phenyl]-N,N-dimethylsulfamide; and N-[4-[[4-(5-chloro-2-hydroxyphenyl)-1,2-dihydro-2-oxo-6-(trifluoromethyl)-3-quinolinyl]thio]phenyl]-4-morpholinepropanesulfonamide;

or a pharmaceutically acceptable salt or solvate thereof.

* * * * *